(12) United States Patent
Sharko et al.

(10) Patent No.: US 9,150,492 B2
(45) Date of Patent: Oct. 6, 2015

(54) NONYL ALCOHOLS WITH A LOW DEGREE OF BRANCHING AND THEIR DERIVATIVES

(75) Inventors: Paul Theodore Sharko, Houston, TX (US); Julian Richard Barnes, Amsterdam (NL); James Grace Crump, Houston, TX (US)

(73) Assignee: Shell Oil Company, Houston, TX (US)

( * ) Notice: Subject to any disclaimer, the term of this patent is extended or adjusted under 35 U.S.C. 154(b) by 735 days.

(21) Appl. No.: 13/482,524

(22) Filed: May 29, 2012

(65) Prior Publication Data

US 2012/0310004 A1 Dec. 6, 2012

Related U.S. Application Data

(60) Provisional application No. 61/492,067, filed on Jun. 1, 2011.

(51) Int. Cl.

| | | |
|---|---|---|
| *C07C 29/32* | (2006.01) | |
| *C07C 29/34* | (2006.01) | |
| *C07C 69/80* | (2006.01) | |
| *C07C 29/14* | (2006.01) | |
| *C07C 43/11* | (2006.01) | |

(52) U.S. Cl.
CPC ................. *C07C 69/80* (2013.01); *C07C 29/14* (2013.01); *C07C 43/11* (2013.01)

(58) Field of Classification Search
CPC ................................ C07C 29/32; C07C 29/34
USPC ........... 568/902; 560/147, 155, 171, 180, 190
See application file for complete search history.

(56) References Cited

U.S. PATENT DOCUMENTS

| | | |
|---|---|---|
| 3,231,621 A | 2/1966 | Gdowik et al. |
| 3,239,566 A | 3/1966 | Slaugh et al. |
| 3,239,569 A | 3/1966 | Slaugh et al. |
| 3,239,570 A | 3/1966 | Slaugh et al. |
| 3,239,571 A | 3/1966 | Slaugh et al. |
| 3,420,898 A | 1/1969 | van Winkle et al. |
| 3,440,291 A | 4/1969 | van Winkle et al. |
| 3,448,157 A | 6/1969 | Slaugh et al. |
| 3,448,158 A | 6/1969 | Slaugh et al. |
| 3,496,203 A | 2/1970 | Morris et al. |
| 3,496,204 A | 2/1970 | Morris et al. |
| 3,501,515 A | 3/1970 | van Winkle et al. |
| 3,527,818 A | 9/1970 | Mason et al. |

*Primary Examiner* — Elvis O Price

(57) ABSTRACT

The invention relates to nonyl alcohols with a low degree of branching and derivatives produced using them. In particular the present invention relates to mixture of primary nonyl alcohols in which at least 80% of the alkyl chains are linear and at least 15% of the alkyl chains are branched at the 2-carbon position and its derivatives. The low degree of branching produces derivatives that are more elongated and less bulky that similar derivatives produced with more highly branched alcohols.

2 Claims, No Drawings

NONYL ALCOHOLS WITH A LOW DEGREE OF BRANCHING AND THEIR DERIVATIVES

PRIORITY CLAIM

The present application claims the benefit to priority of U.S. Provisional Application No. 61/492,067 entitled "Nonyl Alcohols with a Low Degree of Branching and Their Derivatives" filed Jun. 1, 2011.

FIELD OF THE INVENTION

The invention relates to nonyl alcohols with a low degree of branching and derivatives produced using them.

BACKGROUND OF THE INVENTION

Nonyl alcohols are well known and commonly used to synthesize plasticizers and surface active agents. The most common nonyl alcohol is a totally branched nonyl alcohol known as isononyl alcohol. Isononyl alcohol is most commonly produced by dimerizing butene and performing the oxo hydroformylation reaction as described in *Industrial Organic Chemicals*; Wittcoff, Harold A., Reuben, Bryan G., and Plotkin, Jeffrey S., Wiley-Interscience, 2004. This alcohol is sold commercially by ExxonMobil Corporation under the trade name Exxal® 9. A second type of nonyl alcohol is produced by performing the oxo hydroformylation reaction on a linear octene. This yields a nonyl alcohol containing between 35 and 65% branched species.

While both types of nonyl alcohol can be used to synthesize useful derivatives like plasticizers and surface active agents, the high degree of branching limits the functionality of these derivatives. There is a need for a nonyl alcohol that can be produced with a lower proportion of branched species.

SUMMARY OF THE INVENTION

The present invention provides a nonyl alcohol with a low degree of branching and derivatives made therefrom. The more elongated and less bulky molecular character of this nonyl alcohol confers superior characteristics to derivatives derived from it. This is particularly apparent in plasticizer and surface active agent derivatives. Plasticizer derivatives made with this nonyl alcohol exhibit less volatility, more resistance to environmental damage, and superior response to temperature extremes in use, when compared to similar plasticizers produced with more highly branched nonyl alcohols. Surface active agents made with this nonyl alcohol exhibit better detergency and soil adsorption than similar surface active agents made with more highly branched nonyl alcohols. In addition they are more readily biodegraded in the environment.

DETAILED DESCRIPTION OF THE INVENTION

The present invention is a mixture of primary nonyl alcohols in which at least 80% of the alkyl chains are linear and at least 15% of the alkyl chains are branched at the 2-carbon position as well as derivatives of this alcohol. The derivatives include esters of dicarboxylic acids or other polyacids useful as plasticizers as well as alkoxylated alcohols, sulfated alcohols, sulfated alkoxylated alcohols, alcohol ether amines, or other derivatives with hydrophilic moieties useful as surface active agents.

The linear nonyl alcohols have the structure:

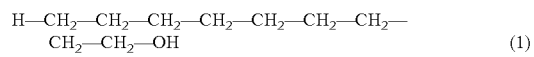

(1)

The branched nonyl alcohols have the general structure:

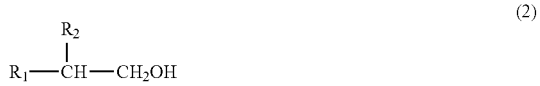

(2)

where $R_1$ and $R_2$ are linear alkyl chains containing a total of 7 carbon atoms between them.

Mixtures having the composition of approximately 82% of structure (1) and 18% of structure (2) can be synthesized from linear octene by the modified Oxo process, using a phosphine, phosphite, arsine, or pyridine ligand modified cobalt or rhodium catalyst, as described in U.S. Pat. Nos. 3,231,621; 3,239,566; 3,239,569; 3,239,570; 3,239,571; 3,420,898; 3,440,291; 3,448,158; 3,448,157; 3,496,203; 3,496,204; 3,501,515; 3,527,818, the disclosures of which are incorporated herein by reference.

Hydroformylation is a term used in the art to denote the reaction of an olefin with CO and $H_2$ to produce an aldehyde/alcohol which has one more carbon atom than the reactant olefin. Frequently in the art the term hydroformylation is utilized to cover the aldehyde and the reduction to the alcohol step in total, i.e., hydroformylation refers to the production of alcohols from olefins via carbonylation and an aldehyde reduction process. As used herein, hydroformylation refers to the ultimate production of alcohols.

Alcohol derivatives useful as plasticizers are well known in the art. Synthesis and properties of common plasticizers are disclosed in *Technology of Plasticizers*; Sears, J. Kern and Darby, Joseph R., John Wiley & Sons, 1982 and references cited therein. The present invention includes plasticizers synthesized from a mixture of primary nonyl alcohols in which at least 80% of the alkyl chains are linear and at least 15% of the alkyl chains are branched at the 2-carbon position. A preferred embodiment of this invention comprises diesters of the novel nonyl alcohol mixture with diacids. Common diacids that can be esterified to produce plasticizers include phthalic acid, adipic acid, sebacic acid, and succinic acid. An additional preferred embodiment of this invention includes polyesters of polyacids containing three or more acid moieties. Common polyacids that can be esterified to produce plasticizers include trimellitic acid and terephthalic acid.

Alcohol derivatives useful as surface active agents are well known in the art. Synthesis and properties of common surface active agents are disclosed in *Handbook of Detergents Part F: Production*, Zoller, Uri and Sosis, Paul CRC Press, 2009 and references cited therein.

The present invention includes surface active agents synthesized from a mixture of primary nonyl alcohols in which at least 80% of the alkyl chains are linear and at least 15% of the alkyl chains are branched at the 2-carbon position. Preferred embodiments of this invention include polyalkoxylates, sulfates, sulfated polyalkoxylates, and ether amines of the novel nonyl alcohol mixture.

EXAMPLE 1

In an air-free environment, 1.5 kg of octene was combined with 67 g of phosphine modified cobalt catalyst and stirred overnight to dissolve. A 1 gallon autoclave was purged with nitrogen and the solution added. The reactor was pressurized with 2/1 ratio of $H_2/CO$ to 6.89 MPa and heated to 200° C. with stirring for 7 hours. The hydroformylated reaction product was vacuum distilled to recover 998 g of the hydroformylated octene.

While stirring and under a constantly flowing dry nitrogen atmosphere, this crude hydroformylated octene was treated with 6.25 g of sodium borohydride to saponify any esters and reduce any aldehydes formed in the hydroformylation reaction. The temperature was raised to 50° C. and held for 3 hours while stirring continued. At the end of 3 hours an additional 6.25 g of sodium borohydride was added. The temperature was raised to 90° C. and held for 3.5 hours under constant stirring. The mixture was allowed to cool and stirring stopped while a dry nitrogen atmosphere was maintained.

The resultant crude alcohol mixture was heated to 80° C., while maintaining constant stirring and a flow of dry nitrogen. Then 100 ml of warm (90° C.) deionized water was added slowly to the crude alcohol mixture. After the first 100 ml of deionized water was added, an additional 400 ml of warm water was added at a slow rate. Stirring was maintained for 30 minutes. Heating and stirring were discontinued and the crude alcohol/water mixture was allowed to separate into 2 phases. The water phase was then removed.

This water-washing step was repeated two additional times. The crude alcohol was then vacuum distilled to separate the mixture of nonyl alcohols from light and heavy by-products. The total yield of mixed nonyl alcohols was 918 g. Approximately 82% of the alkyl chains were linear and 18% were branched at the 2-carbon position.

EXAMPLE 2

567 g of nonyl alcohol produced in Example 1 was combined with 280 g of phthalic anhydride, 200 g of toluene and 5.5 g of methanesulfonic acid. The reaction was set up for reflux through a Dean-Stark trap using a nitrogen purge and slow stirring. The reactor contents were refluxed for 5 hours. Residual catalyst was neutralized with a 10% $NaCO_3$ solution and the product was water washed. The product was purified by vacuum stripping and distillation to yield 818 g of dinonyl phthalate.

EXAMPLE 3

567 g of branched isononyl alcohol (Exxal®9, ExxonMobil Corporation) was treated according to the procedure of Example 2. The reaction yielded 809 g of isononyl phthalate.

Plasticizer Performance

Samples of plasticized PVC were prepared with the plasticizers of Examples 2 and 3. In each case 67 parts of the plasticizer was combined with 100 parts of the PVC resin.

A control sample was also prepared using the plasticizer di(ethylhexyl)phthalate. Several critical physical properties were measured for each sample. In each case the measurement was scaled to the result for the sample plasticized with di(ethylhexyl)phthalate. Results are shown in the tables 1, 2 and 3 below.

TABLE 1

| Property | Volatility (% plasticizer lost in 24 hour at 87° C.) | | |
|---|---|---|---|
| Plasticizer | Di(ethylhexyl)phthalate | Diisononyl phthalate | Dinonyl phthalate |
| Result | 100 | 60 | 43 |

TABLE 2

| Property | Efficiency (Reciprocal of Shore "A" Hardness) | | |
|---|---|---|---|
| Plasticizer | Di(ethylhexyl)phthalate | Diisononyl phthalate | Dinonyl phthalate |
| Result | 100 | 93 | 98 |

TABLE 3

| Property | Low temperature flexibility ($T_f$° C.) | | |
|---|---|---|---|
| Plasticizer: | Di(ethylhexyl)phthalate | Diisononyl phthalate | Dinonyl phthalate |
| Result: | 100 | 108 | 123 |

The volatility result shows that the dinonyl phthalate plasticizer is much more resistant to evaporation than is the diisononyl phthalate. The efficiency result shows that dinonyl phthalate will plasticize PVC to a greater extent than diisononyl phthalate at equal loading. The low temperature flexibility result shows that PVC plasticized with dinonyl phthalate retains flexibility at lower temperature than PVC plasticized with diisononyl phthalate. These three results combine to illustrate the benefits seen when this novel mixed nonyl alcohol is used to produce phthalate derivatives. Similar benefits are expected for other classes of plasticizers as well.

EXAMPLE 4

300 g of nonyl alcohol from Example 1 was purged with dry nitrogen gas for 30 minutes in a flask fitted with a Dean-Stark trap. 1.01 g of KOH was added and the flask was heated to 120° C. for 90 minutes. The contents were transferred to an autoclave and pressurized to 137.9 kPa with nitrogen. The autoclave was heated to 165° C. and 275 g of ethylene oxide was slowly added. The autoclave was maintained at temperature for 2 hours, then cooled and emptied. The excess catalyst was neutralized with 0.92 g of acetic acid. 572 g of nonyl $(EO)_3$ were recovered.

EXAMPLE 5

The procedure of Example 4 was repeated using 1.82 g of KOH, 733 g of ethylene oxide and 1.65 g of acetic acid. 1025 g of nonyl$(EO)_8$ were recovered

EXAMPLE 6

The procedure of Example 4 was repeated using 300 g of branched isononyl alcohol (Exxal®9, ExxonMobil Corporation). 571 g of isononyl$(EO)_3$ were recovered.

EXAMPLE 7

The procedure of Example 4 was repeated using 300 g of branched isononyl alcohol (Exxal®9, ExxonMobil Corporation), 1.82 g of KOH, 733 g of ethylene oxide and 1.65 g of acetic acid. 1026 g of isononyl(EO)$_8$ were recovered Surface Active Agents 1. Hard Surface Cleaning Application The products described in Examples 4-7 were used to create two simple formulations to demonstrate the practical benefits of using surface active agents derived from this novel nonyl alcohol mixture to clean hard surfaces. The composition of the formulations is shown in Table 4.

TABLE 4

|  | Formula 1 | Formula 2 |
| --- | --- | --- |
| Nonyl(EO)$_3$ | 2.0% |  |
| Nonyl(EO)$_8$ | 2.0% |  |
| Isononyl(EO)$_3$ |  | 2.0% |
| Isononyl(EO)$_8$ |  | 2.0% |
| Sodium Carbonate | 0.5% | 0.5% |
| Water | 95.5% | 95.5% |

White vinyl tiles were stained with a standard oily soil prepared in accordance with ASTM D 4828-92. Reflectance measurements on the soiled tiles were conducted. Each tile was sprayed with 5 ml of either Formula 1 or Formula 2 and was wiped three times with a damp sponge. Reflectance measurements of the cleaned areas of the tile were taken. Soil removal was calculated as the difference between the two reflectance measurements divided by the reflectance measurement of the soiled tile. Each formula was tested on 10 tiles and the soil removal numbers were averaged and are shown in Table 5.

TABLE 5

|  | Soil Removal |
| --- | --- |
| Formula 1 | 92% |
| Formula 2 | 67% |

2. Laundry Cleaning Application

The products described in Examples 5 and 7 were used to create two simple formulations to demonstrate the practical benefits of using surface active agents derived from this novel nonyl alcohol mixture in a laundry cleaning application. The composition of the formulations is shown in Table 6.

TABLE 6

|  | Formula 3 | Formula 4 |
| --- | --- | --- |
| (C$_{12}$-C$_{15}$)(EO)$_3$SO$_3$ | 10.0% | 10.0% |
| Nonyl(EO)$_8$ | 5.0% |  |
| Isononyl(EO)$_8$ |  | 5.0% |
| Sodium Citrate | 5.0% | 5.0% |
| Triethanolamine | 5.0% | 5.0% |
| Water | 75.0% | 75.0% |

In this demonstration, 9 test cloths of either 100% cotton or a polyester/cotton blend were soiled with a mixture of dust and synthetic sebum. Each was individually marked and an optical brightness measurement of each was made.

An aqueous solution of the following composition was prepared:

| 2.0 g/l | Formula 3 |
| --- | --- |
| 150 ppm | Ca/Mg water hardness |

The test cloths were washed in this solution in a controlled manner at 20° C., rinsed, and dried. Optical brightness measurements were repeated and the proportion of soil removed from each was calculated from the optical brightness measurements. Soil removal for the 9 test cloths was averaged and the average is reported in the table below.

Another demonstration was performed in the same manner using a solution of the following composition:

| 2.0 g/l | Formula 4 |
| --- | --- |
| 150 ppm | Ca/Mg water hardness |

Soil removal results are reported in Table 7.

TABLE 7

|  | Formula 3 solution | Formula 4 solution |
| --- | --- | --- |
| Soil removal from 100% cotton test cloths | 35.3% | 25.2% |
| Soil removal from polyester/cotton test cloths | 65.3% | 47.5% |

These results show that the detergency of the Formula 3 solution is substantially better than the detergency of the Formula 4 solution, indicating that the surfactant in Example 5 can provide superior cleaning benefits to the surfactant in Example 7 when used in a typical laundry detergent formulation.

This demonstrates the advantage of the novel mixed nonyl alcohol when derivatized to a typical class of surface active agents. Similar advantages are expected when it is derivatized to other classes of surface active agents as well.

What is claimed:

1. A mixture of derivatives of nonyl alcohols produced by derivatizing a mixture of nonyl alcohols comprising at least 80% linear nonyl alcohols and at least 15% of branched nonyl alcohols having branching at the 2-carbon position.

2. A mixture as claimed in claim 1 wherein the derivatives comprise esters of dicarboxylic acids, esters of polycarboxylic acids, alkoxylated alcohols, sulfated alcohols, sulfated alkoxylated alcohols, and alcohol ether amines.

* * * * *